(12) United States Patent
Lin

(10) Patent No.: US 9,468,760 B1
(45) Date of Patent: Oct. 18, 2016

(54) LIGHT-DRIVEN RETINA CHIP

(71) Applicant: Po-Kang Lin, Taipei (TW)

(72) Inventor: Po-Kang Lin, Taipei (TW)

( * ) Notice: Subject to any disclaimer, the term of this patent is extended or adjusted under 35 U.S.C. 154(b) by 0 days.

(21) Appl. No.: 14/840,079

(22) Filed: Aug. 31, 2015

(51) Int. Cl.
*A61N 1/08* (2006.01)
*A61N 1/36* (2006.01)
*G01J 1/44* (2006.01)
*A61N 1/05* (2006.01)
*A61F 2/14* (2006.01)

(52) U.S. Cl.
CPC .............. *A61N 1/36046* (2013.01); *A61F 2/14* (2013.01); *A61N 1/0543* (2013.01); *G01J 1/44* (2013.01); *G01J 2001/444* (2013.01); *G01J 2001/446* (2013.01); *G01J 2001/448* (2013.01)

(58) Field of Classification Search
None
See application file for complete search history.

(56) References Cited

U.S. PATENT DOCUMENTS 8,734,513 B2 * 5/2014 Wu .................... A61N 1/36046
607/54

* cited by examiner

*Primary Examiner* — Brian T Gedeon
(74) *Attorney, Agent, or Firm* — Lin & Associates Intellectual Property, Inc.

(57) ABSTRACT

The present invention provides a light-driven retina chip capable of receiving a signal light and a background light, including: an array of photodiodes and a plurality of background light eliminating units. The array of photodiodes includes a plurality of photodiodes and a plurality of current amplifying circuits. The signal light is converted into an electric signal and the background light is converted into a plurality of background light currents. The photodiodes are correspondingly connected to the current amplifying circuits. The background light eliminating unit includes a plurality of background light sensing circuits and a plurality of current eliminating circuits. The current eliminating circuits are respectively and electrically connected to the photodiodes of the array of photodiodes. The background light currents generated by the photodiodes from the background light are eliminated by the background light eliminating units, thereby enhancing a dynamic range of the light-driven retina chip.

8 Claims, 4 Drawing Sheets

LIGHT-DRIVEN RETINA CHIP

BACKGROUND OF THE INVENTION

1. Field of the Invention

The present invention relates to a retina chip, and more particularly, relates to a light-driven retina chip.

2. The Prior Arts

According to the statistics of World Health Organization (WHO), over 4.5 million of the population in the world is suffering with eye diseases, and the number of population with eye disease is estimated to increase drastically to 7.6 million in 2020.

In a sequence from front to back, the following parts of an eyeball form the structure thereof: cornea, pupil, lens, vitreous body and retina. The light that is focused by the vitreous body is converted into electric signals and chemical signals by the retina first; subsequently, the signals are transmitted to the brain through the optic nerve, thereby allowing human beings to see images.

A retina has a rather complicated structure, which can be substantially divided into three different layers. When the light enters the retina, it is to pass through a clear outer layer and a clear middle layer first before reaching an innermost layer of the photoreceptor cells. The photoreceptor cell will convert the light signal into electric signals and chemical signals, and the converted signals are transmitted to the cells at the middle layer for subsequent processing. Processed signals are then transmitted to the ganglion cells located at the outermost layer first before being transmitted back to the brain.

If the photoreceptor cells of a retina are damaged, one could experience loss of vision. Retinitis pigmentosa and age-related macular degeneration are two types of commonly seen visual disorders, and both of them can be improved with retina chips.

Referring to FIG. 1, a pair of specially crafted glasses 11, which is equipped with a miniature camera 12, must be worn by a user using a conventional retina chip. The miniature camera 12 converts any light signal captured into electric signals, and transmits the electric signals to the processing chip 14 attached next to the ear of the user via the wire 13. The processing chip 14 then converts the electric signals into electric pulse signals, which are readable by the ganglion cells. After the electric pulse signals are encoded, they are transmitted to a decoding chip 15 embedded under the skin at the back of the ear. Subsequently, the decoded signals are transmitted to enter the eyeball via a wire 16, which is embedded under the facial skin and is connected to the eye orbit. Finally, the decoded signals are transmitted to an electrode plate 17 that is attached to the ganglion cells at the outermost layer of the retina. A battery box 18 connected with the pair of specially crafted glasses 11 serves as the power source of the miniature camera 12 and the processing chip 14. As for the electrode plate 17 attached to the retina and the decoding chip 15, electricity can be provided when the signal is transmitted thereto in the form of radio waves.

Referring to FIG. 2, a pair of specially crafted glasses 21 is also required for a user who is using a new generation retina chip. Similarly, the pair of specially crafted glasses 21 is equipped with a miniature camera 22 and a processing chip 23. The processing chip 23 is able to convert the electric signals transmitted by the miniature camera 22 into optical pulse signals, and then directly emit the light pulse signals to an electrode plate 24 that is embedded under the photoreceptor cells. The electrode plate 24 is manufactured with otpoelectrical materials, thus it is able to directly convert light pulse signals into electric pulse signals. The electric pulse signals are then transmitted to the cells at the middle layer of the retina for subsequent processing, and the processed signals are transmitted to the brain by the ganglion cells to be integrated. Since the processing chip 23 is also manufactured with otpoelectrical materials, it can generate electricity upon the receiving of light; as a result, users no longer need to carry a battery box around all the time. Compared with the retina chip described in the above section, the new generation retina chip is much more convenient.

Although the otpoelectrical material based processing chip is able to receive light signals and generate electricity utilizing the received light signals, performing the two functions at the same time is likely to cause failure in the recognition of the light signals, which would further compromise the recognition results of the retina chip. Therefore, it is an urgent need for the industry to develop a retina chip that can generate electricity with light signals while maintaining a high recognition effect.

SUMMARY OF THE INVENTION

Based on the above reasons, a primary objective of the present invention is to provide a light-driven retina chip for resolving the problem of light signal recognition in the conventional retina chips.

For achieving the foregoing objectives, the present invention provides a light-driven retina chip capable of receiving a signal light and a background light, including: an array of photodiodes including a plurality of photodiodes and a plurality of current amplifying circuits, wherein the signal light is converted into an electric signal and the background light is converted into a plurality of background light currents by the photodiodes, the photodiodes are correspondingly connected to the current amplifying circuits, and the electric signal and the background light currents are amplified by the current amplifying circuits of the array of photodiodes; and, a plurality of background light eliminating units including a plurality of background light sensing circuits and a plurality of current eliminating circuits, wherein the current eliminating circuits are respectively and electrically connected to the photodiodes of the array of photodiodes, the electric signal is weighted by the current eliminating circuits, and the background light currents generated by the photodiodes from the background light are eliminated by the background light eliminating units, thereby enhancing a dynamic range of the light-driven retina chip.

Preferably, the light-driven retina chip of the present invention may further include a photoelectric converting module electrically connected to the array of photodiodes and the background eliminating units. The photoelectric converting module converts light energy into electric energy and provides electric energy to the array of photodiodes and the background eliminating units.

Preferably, the light-driven retina chip of the present invention may be installed inside a retina of a user, and the electric signal that has been weighted is sent to neural cells of the retina of the user.

Preferably, the array of photodiodes may be disposed at a central location of the light-driven retina chip.

Preferably, the array of photodiodes may be a 64×64 array of photo diodes.

Preferably, the background light eliminating units may include a first background light eliminating unit, a second background light eliminating unit, a third background light eliminating unit and a fourth background light eliminating unit, and each of the background light eliminating units is respectively disposed at a corner of the light-driven retina chip.

Preferably, the signal light may be one of or a combination of the following: a red signal light, a green signal light and a blue signal light.

Preferably, the background light may be an infrared background light.

Preferably, the photoelectric converting module may be a solar chip module.

The light-driven retina chip of the present invention receives the signal light and the background light in synchronization. Not only can the infrared light and visible light be converted into electricity by the photoelectric converting module for the operation of the array of photodiodes and the background light eliminating units, but the array of photodiodes can also recognize the signal light effectively to generate corresponding simulation currents for the ganglion cells of the retina. When compared with the retina chips of the related art, the light-driven retina chip of the present invention is advantageous in that it has higher efficiency and higher recognition effect.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention. The present invention may also be implemented or applied as other embodiments that are not described herein, and each details described in the specification may also be changed or modified according to different aspects without departing the spirit of the present invention.

It should be noted that the structure, ratio and size shown in the accompanying drawings of the present invention are only for illustrative purposes of the disclosure described in the specification, so those who skilled in the art may have a better understanding of the present invention. The structure, ratio and size shown in the accompanying drawings are not to limit the scope of the present invention; therefore, they do not represent any substantive technical meanings. Any structures modifications, ratios changes or size adjustment made to the drawings should still be considered to be within the scope of the present invention as long as they do not affect the effects and purposes thereof.

Figure 1:
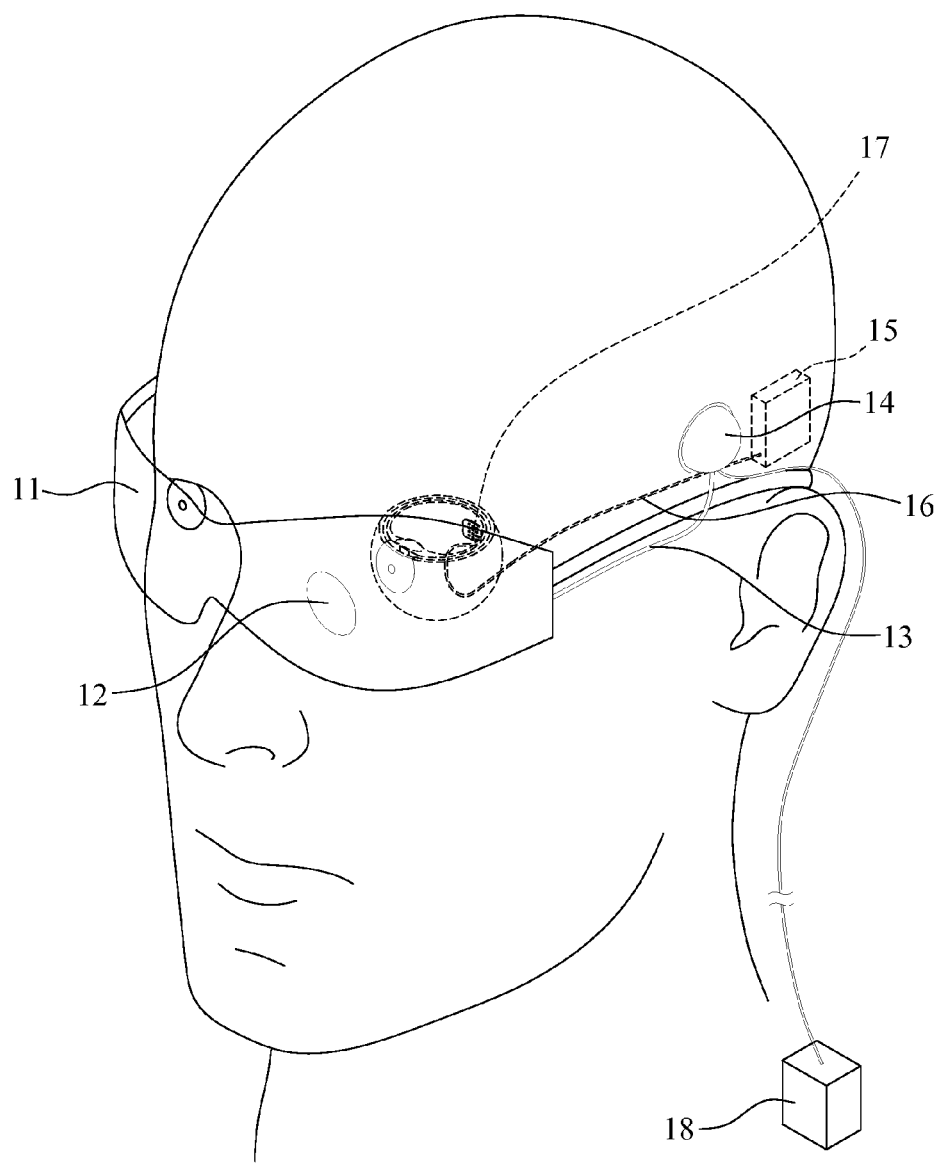
FIG. 1 is a schematic view illustrating a first type of conventional retina chip in use.
Figure 2:
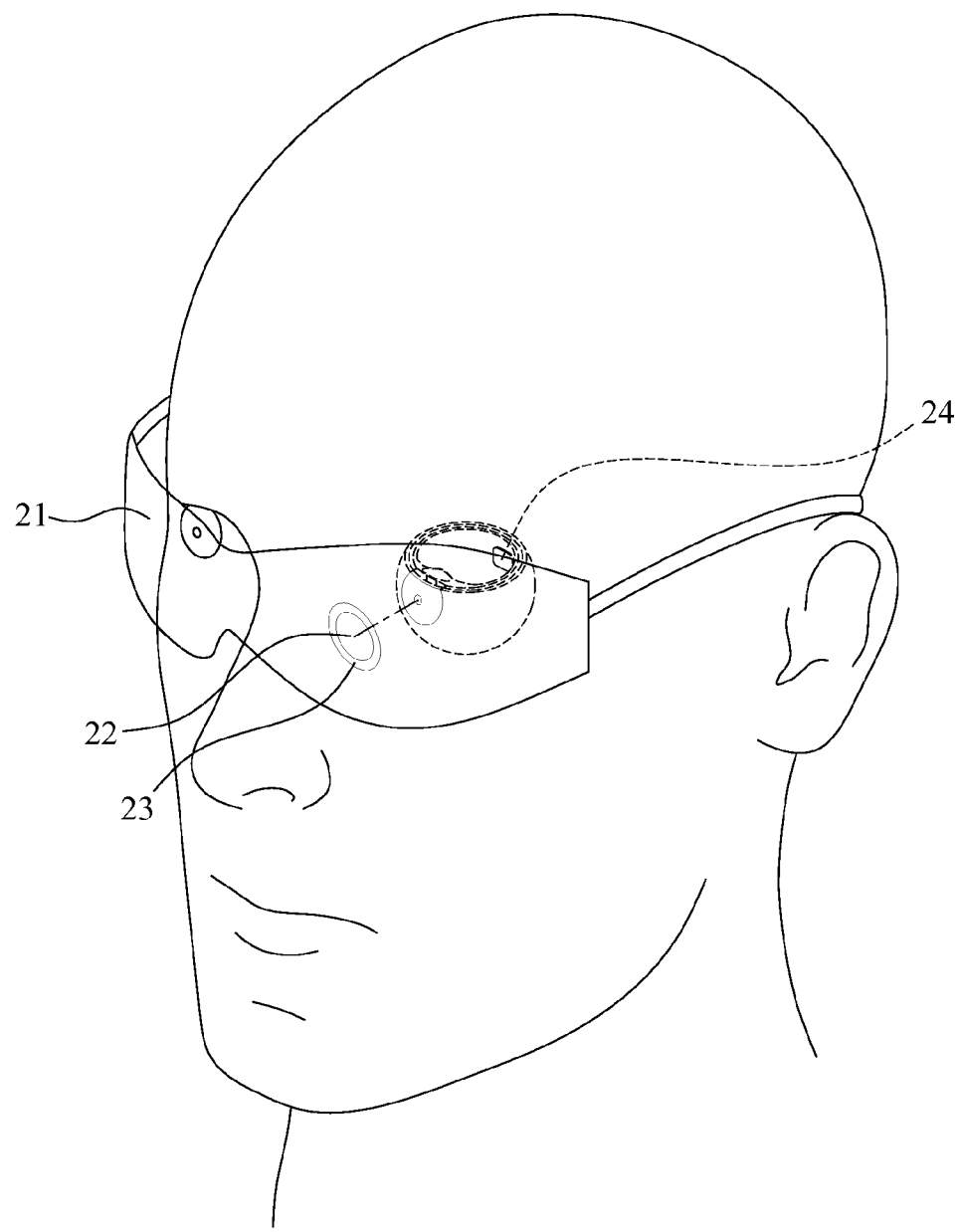
FIG. 2 is a schematic view illustrating a second type of conventional retina chip in use.
Figure 3:
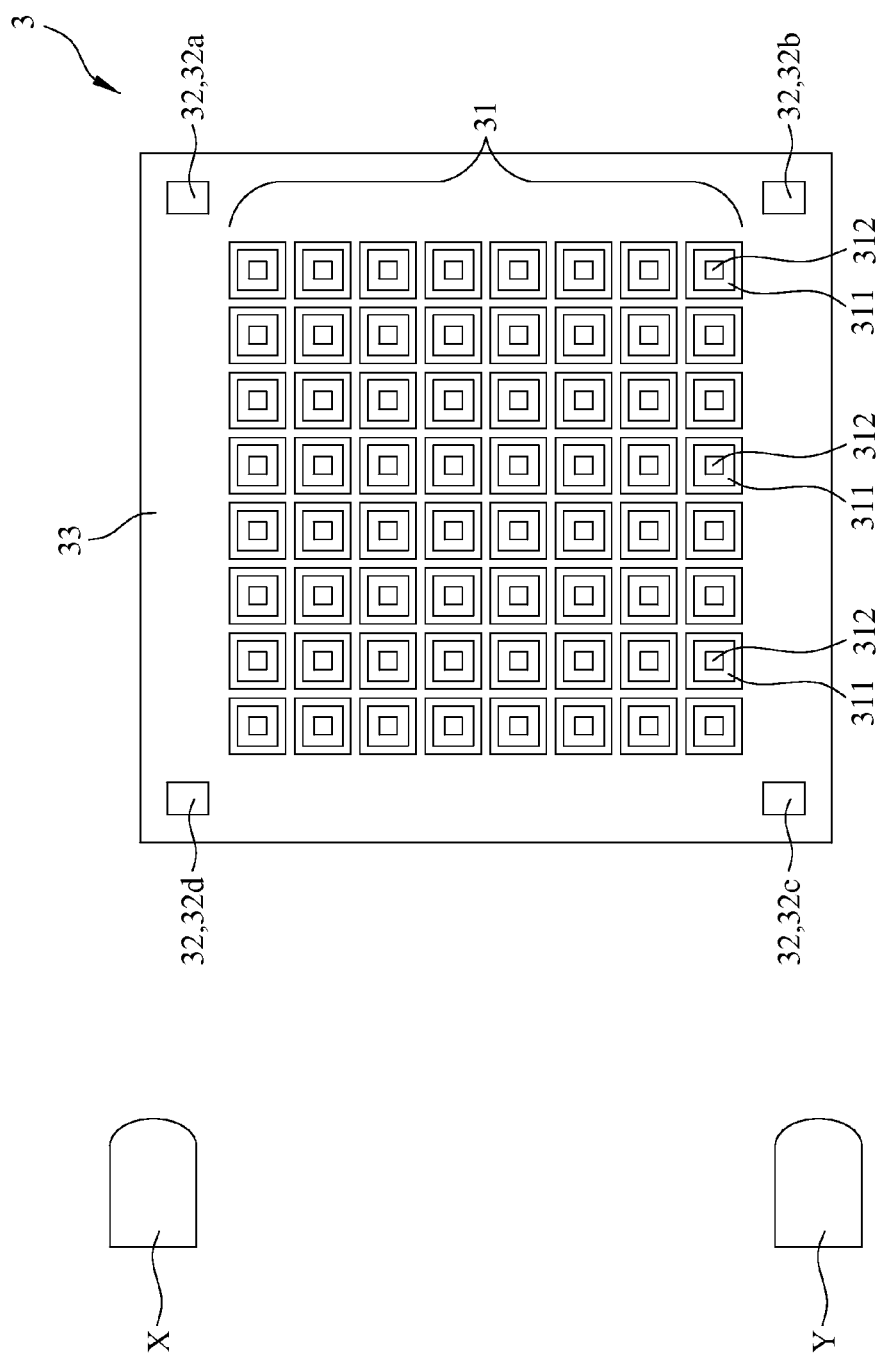
FIG. 3 is a schematic view showing a light-driven retina chip of the present invention.

FIG. 3 is a schematic view showing the light-driven retina chip of the present invention. As shown in FIG. 3, a signal light X and a background light Y are received by the light-driven retina chip 3 of the present invention. The light-driven retina chip 3 includes: an array of photodiodes 31 and a plurality of background light eliminating units 32. The array of photodiodes 31 includes a plurality of photodiodes 311 and a plurality of current amplifying circuits 312. The signal light X is converted into an electric signal and the background light Y is converted into a plurality of background light currents by the photodiodes 311. Each of the photodiodes 311 is correspondingly connected to each current amplifying circuit 312, and the current amplifying circuit 312 of the array of photodiodes 31 amplifies the electric signal and the background light currents. The background light eliminating units 32 include a plurality of background light sensing circuits and a plurality of current eliminating circuits (not shown in the figures). The current eliminating circuits are respectively and electrically connected to the photodiodes 311 of the array of photodiodes 31. The electric signal is weighted by the current eliminating circuits, and the background light currents generated by the photodiodes 311 from the background light Y are eliminated by the background light eliminating units 32, thereby enhancing a dynamic range of the light-driven retina chip 3.

In the embodiment of the present invention, the light-driven retina chip 3 of the present invention further includes a photoelectric converting module 33, which is electrically connected to the array of photodiodes 31 and the background light eliminating units 32. The photoelectric converting module 33 is able to convert the signal light X and the background light Y into electric energy, so the electric energy can be provided to the array of photodiodes 31 and the background eliminating units 32 for the operation thereof.

Figure 4:
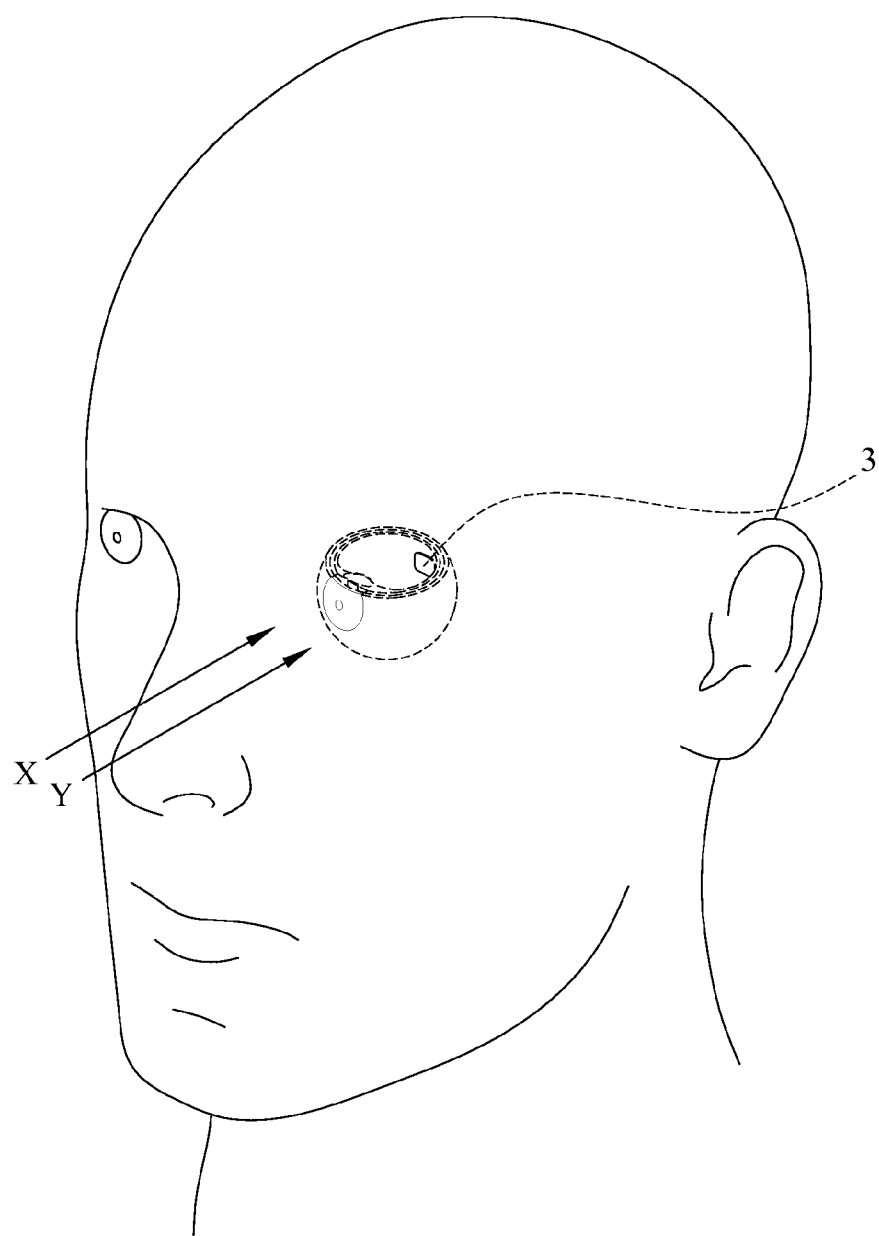
FIG. 4 is a schematic view illustration the light-driven retina chip of the present invention in use.

Next, please refer to FIG. 3 and FIG. 4 at the same time. FIG. 4 is a schematic view illustrating the light-driven retina chip 3 of the present invention in use. In the embodiment of the present invention, the light-driven retina chip 3 can be installed inside a retina of a user, and the weighted electric signal can be transmitted to the ganglion cells of the retina of the user.

As shown in FIG. 3, the array of photodiodes 31 can be disposed at a central location of the light-driven retina chip 3 in the embodiment of the present invention. However, the location of the array of photodiodes 31 is not limited thereto.

In the embodiment of the present invention, the array of photodiodes 31 can be a 64×64 array of photodiodes, but the size of the array is not limited thereto. For example, the array of photodiodes 31 can also be a 128×128 array of photodiodes.

In the present embodiment, the background light eliminating unit 31 may include a first background light eliminating unit 32a, a second background light eliminating unit 32b, a third background light eliminating unit 32c and a fourth background light eliminating unit 32d. Each of the background light eliminating units is disposed at a corner of the light-driven retina chip 3 so as to effectively detect the background light Y.

In the present embodiment, the signal light X may be one of the following: a red signal light, a green signal light and a blue signal light. The signal light X may also be a combination of the abovementioned light, such as an orange signal light, a yellow signal light, an indigo signal light, a purple signal light, and etc.

In the present embodiment, the background light Y can be an infrared background light, but it is not limited thereto. For example, the background light Y may also be an UV light as long as it is harmful to the eyes of the user.

In the present invention, the photoelectric converting module 33 may be a solar chip module, which is able to convert infrared ray and visible lights into electric energy.

The use of solar chip module may be adjusted according to the light-driven retina chip 3 of the present invention, and is not limited thereto.

The light-driven retina chip 3 of the present invention receives the signal light X and the background light Y in synchronization to drive the light-driven retina chip. Not only can the infrared ray and visible lights be converted into electricity by the photoelectric converting module 33 for the operation of the array of photodiodes 31 and the background light eliminating units 32, but the array of photodiodes 31 can also recognize the signal light X effectively to generate corresponding simulation currents for the ganglion cells of the retina. When compared with the conventional retina chips, the light-driven retina chip 3 of the present invention is advantageous in that it has a higher efficiency and higher recognition effect.

Although the present invention has been described with reference to the preferred embodiments thereof, it is apparent to those skilled in the art that a variety of modifications and changes may be made without departing from the scope of the present invention which is intended to be defined by the appended claims. In addition, the number of elements disclosed in the specification is only for illustrative purpose but to limit the scope of the present invention. The scope of the present invention should only be defined by the appended claims.

What is claimed is:

1. A light-driven retina chip capable of receiving a signal light and a background light, said light-driven retina chip comprising:
   an array of photodiodes comprising a plurality of photodiodes and a plurality of current amplifying circuits, wherein the signal light is converted into an electric signal and the background light is converted into a plurality of background light currents by the photodiodes, the photodiodes are correspondingly connected to the current amplifying circuits, and the electric signal and the background light currents are amplified by the current amplifying circuits of the array of photodiodes; and
   a plurality of background light eliminating units comprising a plurality of background light sensing circuits and a plurality of current eliminating circuits, wherein the current eliminating circuits are respectively and electrically connected to the photodiodes of the array of photodiodes, the electric signal is weighted by the current eliminating circuits, and the background light currents generated by the photodiodes from the background light are eliminated by the background light eliminating units, thereby enhancing a dynamic range of the light-driven retina chip;
   wherein the light-driven retina chip is installed inside a retina of a user, and the electric signal that has been weighted is sent to neural cells of the retina of the user.

2. The light-driven retina chip according to claim 1 further comprising a photoelectric converting module electrically connected to the array of photodiodes and the background eliminating units, wherein the photoelectric converting module converts light energy into electric energy and provides electric energy to the array of photodiodes and the background eliminating units.

3. The light-driven retina chip according to claim 2, wherein the photoelectric converting module is a solar chip module.

4. The light-driven retina chip according to claim 1, wherein the array of photodiodes is disposed at a central location of the light-driven retina chip.

5. The light-driven retina chip according to claim 1, wherein the array of photodiodes is a 64×64 array of photodiodes.

6. The light-driven retina chip according to claim 1, wherein the background light eliminating units comprises a first background light eliminating unit, a second background light eliminating unit, a third background light eliminating unit and a fourth background light eliminating unit, and each of the background light eliminating units is respectively disposed at a corner of the light-driven retina chip.

7. The light-driven retina chip according to claim 1, wherein the signal light is one of or a combination of the following: a red signal light, a green signal light and a blue signal light.

8. The light-driven retina chip according to claim 1, wherein the background light is an infrared background light.

* * * * *